US00PP28180P3

(12) United States Plant Patent
Pieters

(10) Patent No.: US PP28,180 P3
(45) Date of Patent: Jul. 11, 2017

(54) ***CHRYSANTHEMUM* PLANT NAMED 'VIGORELLI DARK ORANGE'**

(50) Latin Name: *Chrysanthemum×morifolium*
Varietal Denomination: Vigorelli Dark Orange

(71) Applicant: Dirk Pieters, Oostnieuwkerke (BE)

(72) Inventor: Dirk Pieters, Oostnieuwkerke (BE)

(73) Assignee: Paraty B.V.B.A., Oostnieuwkerke (BE)

( * ) Notice: Subject to any disclaimer, the term of this patent is extended or adjusted under 35 U.S.C. 154(b) by 141 days.

(21) Appl. No.: 14/545,964

(22) Filed: Jul. 10, 2015

(65) Prior Publication Data

US 2017/0013756 P1 Jan. 12, 2017

(51) Int. Cl.
*A01H 5/02* (2006.01)

(52) U.S. Cl.
USPC ..... Plt./290

(58) Field of Classification Search
USPC ..... Plt./263.1, 286, 287, 290
See application file for complete search history.

*Primary Examiner* — Susan McCormick Ewoldt
*Assistant Examiner* — Karen Redden
(74) *Attorney, Agent, or Firm* — C. A. Whealy

(57) ABSTRACT

A new and distinct cultivar of *Chrysanthemum* plant named 'Vigorelli Dark Orange', characterized by its upright, outwardly spreading and uniformly rounded plant habit; vigorous growth habit; dark green-colored leaves; uniform and freely flowering habit; and relatively large decorative-type inflorescences with ray florets that are initially dark red in color becoming dark orange and lighter orange in color with subsequent development giving the inflorescences a bi-colored appearance.

1 Drawing Sheet

Botanical designation: *Chrysanthemum×morifolium.*
Cultivar denomination: 'VIGORELLI DARK ORANGE'.

BACKGROUND OF THE INVENTION

The present invention relates to a new and distinct cultivar of *Chrysanthemum* plant, botanically known as *Chrysanthemum×morifolium* and hereinafter referred to by the name 'Vigorelli Dark Orange'.

The new *Chrysanthemum* plant is a product of a planned breeding program conducted by the Inventor in Oostnieuwkerke, Belgium. The objective of the breeding program is to create new uniformly mounding and freely flowering *Chrysanthemum* plants with unique and attractive ray floret coloration.

The new *Chrysanthemum* plant is a naturally-occurring whole plant mutation of *Chrysanthemum×morifolium* 'Vigorelli Orange', not patented. The new *Chrysanthemum* plant was discovered and selected by the Inventor as a single flowering plant from within a population of plants of 'Vigorelli Orange' in a controlled greenhouse environment in Oostnieuwkerke, Belgium in October, 2012.

Asexual reproduction of the new *Chrysanthemum* plant by vegetative terminal cuttings was first conducted in a controlled greenhouse environment in Oostnieuwkerke, Belgium in January, 2013. Asexual reproduction by vegetative terminal cuttings has shown that the unique features of this new *Chrysanthemum* plant are stable and reproduced true to type in successive generations.

SUMMARY OF THE INVENTION

Plants of the new *Chrysanthemum* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Vigorelli Dark Orange'. These characteristics in combination distinguish 'Vigorelli Dark Orange' as a new and distinct *Chrysanthemum* plant:

1. Upright, outwardly spreading and uniformly rounded plant habit.
2. Vigorous growth habit.
3. Dark green-colored leaves.
4. Uniform and freely flowering habit.
5. Relatively large decorative-type inflorescences with ray florets that are initially dark red in color becoming dark orange and lighter orange in color with subsequent development giving the inflorescences a bi-colored appearance.

Plants of the new *Chrysanthemum* differ primarily from the parent, 'Vigorelli Orange', in the following characteristics:

1. Plants of the new *Chrysanthemum* are not as compact as plants of 'Vigorelli Orange'.
2. Plants of the new *Chrysanthemum* and 'Vigorelli Orange' differ in ray floret color as plants of the new *Chrysanthemum* have darker orange-colored ray florets than plants of 'Vigorelli Orange'.

Plants of the new *Chrysanthemum* can be compared to plants of *Chrysanthemum×morifolium* 'PPP COL OR07', disclosed in U.S. Plant Pat. No. 20,355. In side-by-side comparisons conducted in Oostnieuwkerke, Belgium, plants of the new *Chrysanthemum* differed from plants of 'PPP COL OR07' in the following characteristics:

1. Plants of the new *Chrysanthemum* were smaller than plants of 'PPP COL OR07'.

2. Leaves of plants of the new *Chrysanthemum* were brighter green in color than leaves of plants of 'PPP COL OR07'.
3. Plants of the new *Chrysanthemum* had larger inflorescences than plants of 'PPP COL OR07'.
4. Plants of the new *Chrysanthemum* flowered later than plants of 'PPP COL OR07'.

BRIEF DESCRIPTION OF THE PHOTOGRAPH

The accompanying photograph illustrates the overall appearance of the new *Chrysanthemum* plant showing the colors as true as it is reasonably possible to obtain in colored reproductions of this type. Colors in the photograph may differ slightly from the color values cited in the detailed botanical description which accurately describe the colors of the new *Chrysanthemum* plant.

The photograph comprises a side perspective view of a typical flowering plant of 'Vigorelli Dark Orange' grown in a container.

DETAILED BOTANICAL DESCRIPTION

The aforementioned photograph and following observations and measurements describe plants grown in 19-cm containers in an outdoor nursery in Oostnieuwkerke, Belgium during the spring and summer and under cultural practices generally used in commercial *Chrysanthemum* production. During the production of the plants, day temperatures ranged from 18° C. to 21° C. and night temperatures ranged from 10° C. to 15° C. Plants were 20 weeks old when the photograph and description were taken. In the following description, color references are made to The Royal Horticultural Society Colour Chart, 2005 Edition, except where general terms of ordinary dictionary significance are used.

Botanical classification: *Chrysanthemum×morifolium* 'Vigorelli Dark Orange'.

Parentage: Naturally-occurring whole plant mutation of *Chrysanthemum×morifolium* 'Vigorelli Orange', not patented.

Propagation:

*Type.*—Vegetative terminal cuttings.

*Time to initiate roots, summer.*—About 14 days at temperatures about 20° C.

*Time to initiate roots, winter.*—About 20 days at temperatures about 20° C.

*Time to produce a rooted young plant, summer.*—About 30 days at temperatures about 20° C.

*Time to produce a rooted young plant, winter.*—About 40 days at temperatures about 20° C.

*Root description.*—Fine, fibrous; typically light brown in color, actual color of the roots dependent on substrate composition, water quality, fertilizers, substrate temperature and age of roots.

*Rooting habit.*—Freely branching; medium density.

Plant description:

*Appearance.*—Perennial decorative-type *Chrysanthemum;* stems upright and outwardly spreading giving a uniformly rounded appearance to the plant; plants nearly spherical in overall shape; very freely branching habit, about 25 primary lateral branches develop, each primary lateral branch with multiple secondary branches; pinching enhances lateral branch development; dense and full plant habit; strong and vigorous growth habit.

*Plant height.*—About 50 cm.

*Plant width.*—About 65 cm.

*Lateral branches.*—Length: About 25 cm. Diameter: About 2 mm to 3 mm. Internode length: About 2 cm to 2.5 cm. Strength: Strong, flexible. Aspect: Upright to outwardly spreading. Texture: Pubescent; longitudinally ridged. Luster: Matte. Color: Close to 144A.

*Leaves.*—Arrangement: Alternate, simple. Length: About 5.5 cm to 7 cm. Width: About 3.5 cm to 4 cm. Apex: Rounded to cuspidate. Base: Attenuate. Margin: Palmately lobed and serrate, sinuses between lateral lobes divergent to parallel. Texture, upper and lower surfaces: Slightly pubescent. Luster, upper and lower surfaces: Matte. Color: Developing and fully expanded leaves, upper surface: Close to 136A; venation, close to 148C. Developing and fully expanded leaves, lower surface: Close to 137A; venation, close to 147B to 147C. Petioles: Length: About 1 cm. Diameter: About 2 mm. Texture, upper and lower surfaces: Slightly pubescent and slightly rough. Luster, upper and lower surfaces: Matte. Color, upper surface: Close to 146C. Color, lower surface: Close to 146D.

Inflorescence description:

*Appearance.*—Decorative-type inflorescence form; inflorescences borne on terminals above foliar plane; disc and ray florets arranged acropetally on a capitulum.

*Fragrance.*—Faintly fragrant, pungent.

*Flowering time.*—Under natural season conditions, plants flower in early October in Belgium.

*Postproduction longevity.*—Inflorescences maintain good color and substance for about five weeks on the plant grown in an outdoor nursery; inflorescences persistent.

*Quantity of inflorescences.*—Freely flowering habit with about 20 inflorescences developing per lateral branch with numerous inflorescences developing per plant.

*Inflorescence buds.*—Height: About 5 mm. Diameter: About 8 mm. Shape: Globular. Texture: Smooth. Color: Close to 144A and 137C.

*Inflorescence size and shape.*—Diameter: Relatively large, about 5 cm to 5.5 cm. Depth (height): About 4 cm. Disc diameter: About 1 mm. Shape: Circular; raised dome. Receptacle diameter: About 3 mm. Receptacle height: About 2.5 mm to 3 mm. Receptacle texture: Smooth, glabrous. Receptacle color: Close to 144B.

*Ray florets.*—Quantity and arrangement: About 200 or more ray florets per inflorescence arranged in about ten whorls. Length: About 3 cm to 4 cm. Width: About 6 mm. Shape: Oval. Apex: Rounded. Base: Attenuate. Margin: Entire. Aspect: Mostly flat. Texture, upper and lower surfaces: Smooth, glabrous. Luster, upper and lower surfaces: Matte. Color: When opening, upper surface: Close to 53A. When opening, lower surface: Close to 179A. Fully opened, upper surface: Close to 169C; color becoming closer to 24A with development. Fully opened, lower surface: Close to 34D; color becoming closer to 20B with development.

*Disc florets.*—Quantity and arrangement: About 20 or less disc florets per inflorescence and massed at the center of the receptacle; disc florets inconspicuous. Length: About 3 mm. Diameter: About 0.5 mm to 1 mm. Shape: Tubular, elongated; apices acute. Color, immature: Apex: Close to 144C. Mid-section: Close to 5B. Base: Close to 145D. Color, mature: Apex: Close to 12A. Mid-section: Close to 12A. Base: Close to 12A.

*Phyllaries.*—Quantity and arrangement: About 25 phyllaries per inflorescence arranged in about two or three whorls. Length: About 4 mm to 6 mm. Width: About 2 mm to 3 mm. Shape: Ovate. Apex: Rounded. Base: Rounded to truncate. Margin: Entire. Texture, upper and lower surfaces: Smooth, glabrous. Luster, upper and lower surfaces: Matte. Color, upper surface: Close to 137A. Color, lower surface: Close to N137B.

*Peduncles.*—Length, terminal peduncle: About 4 cm. Length, fourth peduncle: About 6 cm. Length, seventh peduncle: About 8 cm. Diameter: About 2 mm. Angle: About 30° from vertical. Strength: Moderately strong. Texture: Slightly pubescent. Luster: Matte. Color: Close to 146B.

*Reproductive organs.*—Androecium: None observed. Gynoecium: None observed.

*Seeds and fruit.*—Seed and fruit production have not been observed on plants of the new *Chrysanthemum.*

Disease & pest resistance: Resistance to pathogens and pests common to *Chrysanthemum* plants has not been observed on plants of the new *Chrysanthemum* grown under commercial production conditions.

Garden performance: Plants of the new *Chrysanthemum* have demonstrated excellent garden performance and will tolerate temperatures ranging from about 0° C. to about 45° C.

It is claimed:

1. A new and distinct *Chrysanthemum* plant named 'Vigorelli Dark Orange' as illustrated and described.

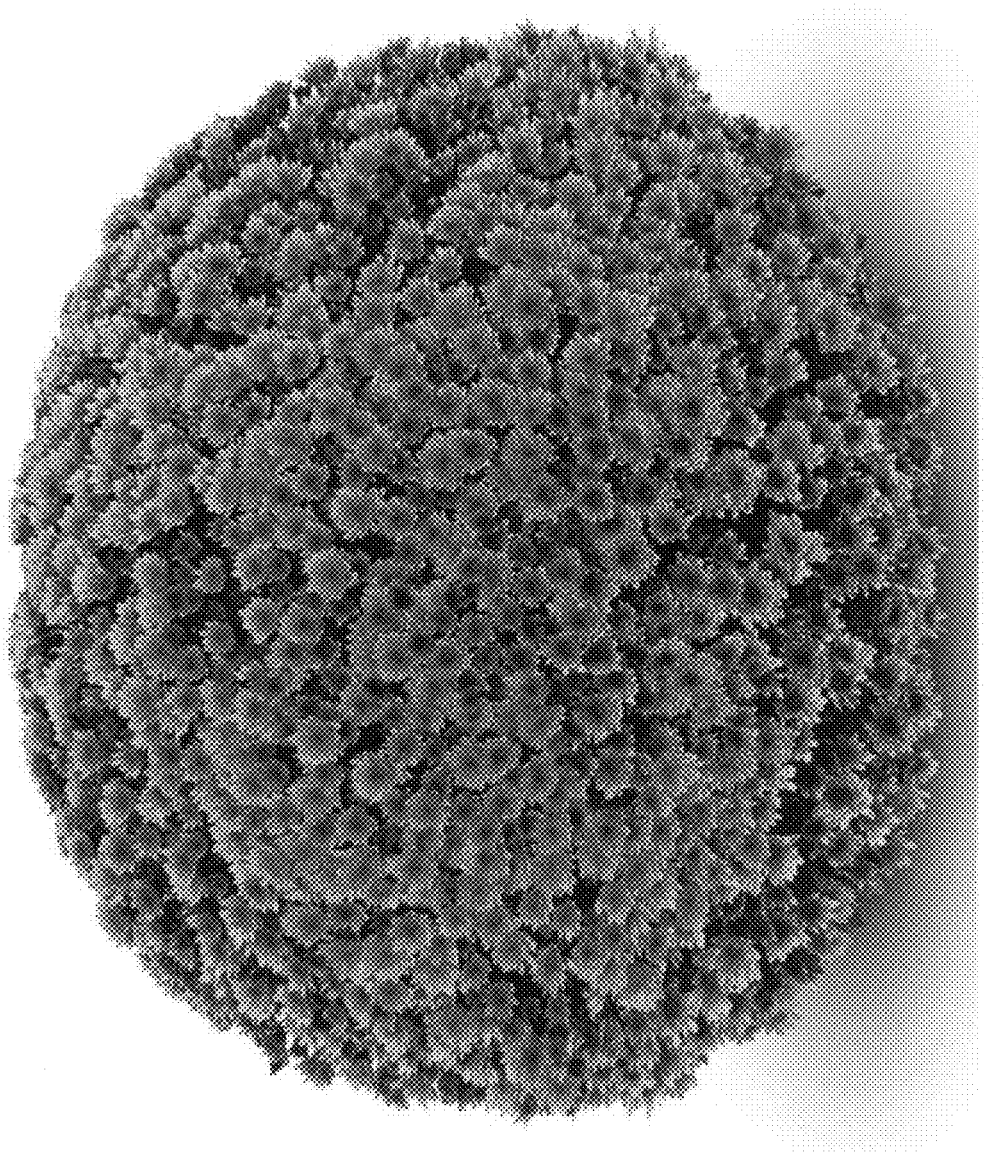

* * * * *